(12) United States Patent
Ezeoke et al.

(10) Patent No.: US 11,819,608 B2
(45) Date of Patent: Nov. 21, 2023

(54) ELECTRONIC AEROSOL PROVISION SYSTEM

(71) Applicant: NICOVENTURES TRADING LIMITED, London (GB)

(72) Inventors: Maurice Ezeoke, London (GB); David Leadley, London (GB); Martin Conrad Mullin, London (GB)

(73) Assignee: Nicoventures Trading Limited, London (GB)

( * ) Notice: Subject to any disclaimer, the term of this patent is extended or adjusted under 35 U.S.C. 154(b) by 516 days.

(21) Appl. No.: 15/733,293

(22) PCT Filed: Dec. 19, 2018

(86) PCT No.: PCT/GB2018/053684
§ 371 (c)(1),
(2) Date: Jun. 22, 2020

(87) PCT Pub. No.: WO2019/122868
PCT Pub. Date: Jun. 27, 2019

(65) Prior Publication Data
US 2021/0106774 A1    Apr. 15, 2021

(30) Foreign Application Priority Data

Dec. 22, 2017 (GB) ..................................... 1721821

(51) Int. Cl.
*A61M 15/06* (2006.01)
*A24F 40/40* (2020.01)
(Continued)

(52) U.S. Cl.
CPC .............. *A61M 15/06* (2013.01); *A24F 40/40* (2020.01); *A24F 40/51* (2020.01); *A24F 40/53* (2020.01);
(Continued)

(58) Field of Classification Search
CPC ................ A61M 15/06; A61M 11/042; A61M 2205/3331; A24F 40/40; A24F 40/51;
(Continued)

(56) References Cited

U.S. PATENT DOCUMENTS 2,057,353 A    10/1936    Whittemore
4,947,875 A    8/1990    Brooks et al.
(Continued)

FOREIGN PATENT DOCUMENTS

CA    2641869 A1    5/2010
CN    1280661 A    1/2001
(Continued)

OTHER PUBLICATIONS

Application and File History for U.S. Appl. No. 14/401,501, filed Nov. 14, 2014, Inventor: Lord, 404 pages.
(Continued)

*Primary Examiner* — Tai T Nguyen
(74) *Attorney, Agent, or Firm* — Patterson Thuente P.A.

(57) ABSTRACT

There is provided a connector configured to be retrofitted to an electronic aerosol provision system including a first connecting interface connectable to a vaporizer for vaporizing liquid for inhalation by a user; a second connecting interface connectable to a power supply for supplying power to the vaporizer; a sensor for sensing a parameter indicative of a change in the electronic aerosol provision system; and a control unit connected to the sensor and configured to output a signal based on the information from the sensor, wherein the connector, when connected to a vaporizer and to a power supply, forms an electronic aerosol provision system.

19 Claims, 5 Drawing Sheets

(51) Int. Cl.
  *A24F 40/51* (2020.01)
  *A24F 40/53* (2020.01)
  *A24F 40/60* (2020.01)
  *A24F 40/65* (2020.01)
  *A61M 11/04* (2006.01)
  *A24F 40/10* (2020.01)

(52) U.S. Cl.
  CPC .............. *A24F 40/60* (2020.01); *A24F 40/65* (2020.01); *A61M 11/042* (2014.02); *A24F 40/10* (2020.01); *A61M 2205/3331* (2013.01); *A61M 2205/3553* (2013.01); *A61M 2205/502* (2013.01); *A61M 2205/581* (2013.01); *A61M 2205/582* (2013.01); *A61M 2205/587* (2013.01); *A61M 2205/8206* (2013.01)

(58) Field of Classification Search
  CPC .......... A24F 40/53; A24F 40/06; A24F 40/65; A24F 40/10
  USPC .................................................... 128/202.21
  See application file for complete search history.

(56) References Cited

U.S. PATENT DOCUMENTS

| | | |
|---|---|---|
| 5,095,921 A | 3/1992 | Losee et al. |
| 5,144,962 A | 9/1992 | Counts et al. |
| 5,372,148 A | 12/1994 | McCafferty et al. |
| 5,661,470 A | 8/1997 | Karr |
| 5,894,841 A | 4/1999 | Voges |
| 6,183,425 B1 | 2/2001 | Whalen et al. |
| 6,196,218 B1 | 3/2001 | Voges |
| 6,615,840 B1 | 9/2003 | Fournier et al. |
| 6,958,691 B1 | 10/2005 | Anderson et al. |
| 7,726,320 B2 | 6/2010 | Robinson et al. |
| 7,726,329 B2 | 6/2010 | Armiroli et al. |
| 7,852,041 B2 | 12/2010 | Lam |
| 8,499,766 B1 | 8/2013 | Newton |
| 8,550,069 B2 | 10/2013 | Alelov |
| 8,674,656 B2 | 3/2014 | Iio et al. |
| 8,997,753 B2 | 4/2015 | Li et al. |
| 9,032,968 B2 | 5/2015 | Glasberg et al. |
| 9,289,014 B2 | 3/2016 | Tucker et al. |
| 9,451,791 B2 | 9/2016 | Sears et al. |
| 9,462,832 B2 | 10/2016 | Lord |
| 9,497,999 B2 | 11/2016 | Lord |
| 9,597,466 B2 | 3/2017 | Henry, Jr. et al. |
| 9,905,175 B2 | 2/2018 | Lee et al. |
| 11,291,252 B2 * | 4/2022 | Sur ..................... H04B 5/0081 |
| 2003/0033055 A1 | 2/2003 | McRae et al. |
| 2003/0123328 A1 | 7/2003 | Guanter |
| 2003/0179003 A1 | 9/2003 | Toda et al. |
| 2003/0226837 A1 | 12/2003 | Blake et al. |
| 2004/0149297 A1 | 8/2004 | Sharpe |
| 2005/0016550 A1 | 1/2005 | Katase |
| 2005/0031148 A1 | 2/2005 | McNary |
| 2005/0045193 A1 | 3/2005 | Yang |
| 2005/0058441 A1 | 3/2005 | Kameyama et al. |
| 2005/0067503 A1 | 3/2005 | Katase |
| 2005/0143866 A1 | 6/2005 | McRae et al. |
| 2005/0166076 A1 | 7/2005 | Truong |
| 2005/0268911 A1 | 12/2005 | Cross et al. |
| 2006/0047368 A1 | 3/2006 | Maharajh et al. |
| 2007/0045288 A1 | 3/2007 | Nelson |
| 2007/0267031 A1 | 11/2007 | Hon |
| 2008/0257367 A1 | 10/2008 | Paterno et al. |
| 2009/0058578 A1 | 3/2009 | Huang |
| 2009/0072783 A1 | 3/2009 | Gaspar et al. |
| 2009/0095292 A1 | 4/2009 | Hamano et al. |
| 2009/0095311 A1 | 4/2009 | Han |
| 2009/0115745 A1 | 5/2009 | Chuang et al. |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2010/0011234 A1 | 1/2010 | Malik et al. |
| 2010/0052660 A1 | 3/2010 | Wang |
| 2010/0109889 A1 | 5/2010 | Deng |
| 2010/0171461 A1 | 7/2010 | Baarman et al. |
| 2010/0194335 A1 | 8/2010 | Kirby et al. |
| 2010/0242974 A1 | 9/2010 | Pan |
| 2010/0289499 A1 | 11/2010 | Bremmer et al. |
| 2010/0313901 A1 | 12/2010 | Fernando et al. |
| 2011/0036346 A1 | 2/2011 | Cohen et al. |
| 2011/0113368 A1 | 5/2011 | Carvajal et al. |
| 2011/0210746 A1 | 9/2011 | Yugou et al. |
| 2011/0226236 A1 | 9/2011 | Buchberger |
| 2011/0226266 A1 | 9/2011 | Tao |
| 2011/0265806 A1 | 11/2011 | Alarcon et al. |
| 2011/0304282 A1 | 12/2011 | Li et al. |
| 2012/0048266 A1 | 3/2012 | Alelov |
| 2012/0170177 A1 | 7/2012 | Pertuit et al. |
| 2012/0227753 A1 | 9/2012 | Newton |
| 2012/0318882 A1 | 12/2012 | Abehasera |
| 2012/0325228 A1 | 12/2012 | Williams |
| 2013/0037041 A1 | 2/2013 | Worm et al. |
| 2013/0042865 A1 | 2/2013 | Monsees et al. |
| 2013/0104916 A1 | 5/2013 | Bellinger et al. |
| 2013/0169230 A1 | 7/2013 | Li et al. |
| 2013/0192615 A1 | 8/2013 | Tucker et al. |
| 2013/0207455 A1 | 8/2013 | Doljack |
| 2013/0220315 A1 | 8/2013 | Conley et al. |
| 2013/0228191 A1 | 9/2013 | Newton |
| 2013/0253427 A1 | 9/2013 | Cerman et al. |
| 2013/0255702 A1 | 10/2013 | Griffith, Jr. et al. |
| 2013/0284192 A1 | 10/2013 | Peleg et al. |
| 2013/0340775 A1 | 12/2013 | Juster et al. |
| 2014/0034071 A1 * | 2/2014 | Levitz ..................... A24F 40/90 |
| | | 131/329 |
| 2014/0053858 A1 | 2/2014 | Liu |
| 2014/0123990 A1 | 5/2014 | Timmermans |
| 2014/0144453 A1 | 5/2014 | Capuano et al. |
| 2014/0283857 A1 | 9/2014 | Liu |
| 2014/0353856 A1 | 12/2014 | Dubief |
| 2015/0020825 A1 * | 1/2015 | Galloway ................ G08B 6/00 |
| | | 340/407.1 |
| 2015/0047661 A1 | 2/2015 | Blackley et al. |
| 2015/0075546 A1 | 3/2015 | Kueny et al. |
| 2015/0114408 A1 | 4/2015 | Lord |
| 2015/0128965 A1 | 5/2015 | Lord |
| 2015/0128966 A1 | 5/2015 | Lord |
| 2015/0128972 A1 | 5/2015 | Verleur et al. |
| 2015/0136153 A1 | 5/2015 | Lord |
| 2015/0164141 A1 | 6/2015 | Newton |
| 2015/0237917 A1 | 8/2015 | Lord |
| 2015/0245660 A1 | 9/2015 | Lord |
| 2015/0257448 A1 | 9/2015 | Lord |
| 2015/0336689 A1 | 11/2015 | Brown et al. |
| 2016/0029695 A1 | 2/2016 | Benites et al. |
| 2016/0049804 A1 | 2/2016 | Lee et al. |
| 2016/0206000 A1 | 7/2016 | Lord et al. |
| 2016/0226286 A1 | 8/2016 | Xiang |
| 2016/0227842 A1 * | 8/2016 | Xiang ..................... A24F 40/40 |
| 2016/0242466 A1 | 8/2016 | Lord et al. |
| 2017/0035114 A1 | 2/2017 | Lord |
| 2021/0112875 A1 * | 4/2021 | Liao ....................... A24F 40/42 |

FOREIGN PATENT DOCUMENTS

| | | |
|---|---|---|
| CN | 2602620 Y | 2/2004 |
| CN | 1284493 C | 11/2006 |
| CN | 201029436 Y | 3/2008 |
| CN | 201238610 Y | 5/2009 |
| CN | 101518361 A | 9/2009 |
| CN | 101557728 A | 10/2009 |
| CN | 100566769 C | 12/2009 |
| CN | 201379072 Y | 1/2010 |
| CN | 201393548 Y | 2/2010 |
| CN | 101969800 A | 2/2011 |
| CN | 101977522 A | 2/2011 |
| CN | 201821914 U | 5/2011 |
| CN | 201830899 U | 5/2011 |
| CN | 102264251 A | 11/2011 |
| CN | 102298435 A | 12/2011 |

(56) References Cited

FOREIGN PATENT DOCUMENTS

| | | |
|---|---|---|
| CN | 202474905 U | 10/2012 |
| CN | 102934843 A | 2/2013 |
| CN | 102970885 A | 3/2013 |
| CN | 202890466 U | 4/2013 |
| CN | 203070141 U | 7/2013 |
| CN | 103237468 A | 8/2013 |
| CN | 203504217 U | 3/2014 |
| DE | 202005018998 U1 | 2/2006 |
| DE | 102010032587 A1 | 2/2011 |
| EP | 1712178 A2 | 10/2006 |
| EP | 2100525 A1 | 9/2009 |
| EP | 2110034 A1 | 10/2009 |
| EP | 2201850 A1 | 6/2010 |
| EP | 2383861 A2 | 11/2011 |
| EP | 2404515 A1 | 1/2012 |
| EP | 2460423 A1 | 6/2012 |
| EP | 2468118 A1 | 6/2012 |
| GB | 2468932 A | 9/2010 |
| GB | 2502053 A | 11/2013 |
| GB | 2502055 A | 11/2013 |
| GB | 2502162 A | 11/2013 |
| GB | 2502163 A | 11/2013 |
| GB | 2502164 A | 11/2013 |
| JP | H05307439 A | 11/1993 |
| JP | H10320082 A | 12/1998 |
| JP | 2006018057 A | 1/2006 |
| JP | 2006338178 A | 12/2006 |
| JP | 2011087569 A | 5/2011 |
| JP | 2012090427 A | 5/2012 |
| KR | 20110002227 U | 3/2011 |
| RU | 2336001 C2 | 10/2008 |
| RU | 2336002 C2 | 10/2008 |
| RU | 2360583 C1 | 7/2009 |
| RU | 94815 U1 | 6/2010 |
| WO | WO-9118860 A1 | 12/1991 |
| WO | WO-9418860 A1 | 9/1994 |
| WO | WO-9501137 A1 | 1/1995 |
| WO | WO-9817130 A1 | 4/1998 |
| WO | WO-9817131 A1 | 4/1998 |
| WO | WO-0050111 A1 | 8/2000 |
| WO | WO-0064517 A1 | 11/2000 |
| WO | WO-2004041007 A2 | 5/2004 |
| WO | WO-2004080216 A1 | 9/2004 |
| WO | WO-2004095955 A1 | 11/2004 |
| WO | WO-2007074430 A1 | 7/2007 |
| WO | WO-2009032064 A2 | 3/2009 |
| WO | WO-2009118085 A1 | 10/2009 |
| WO | WO-2010040015 A2 | 4/2010 |
| WO | WO-2010091593 A1 | 8/2010 |
| WO | WO-2010118644 A1 | 10/2010 |
| WO | WO-2010145805 A1 | 12/2010 |
| WO | WO-2011137453 A2 | 11/2011 |
| WO | WO-2011147699 A1 | 12/2011 |
| WO | WO-2012048266 A1 | 4/2012 |
| WO | WO-2012065754 A2 | 5/2012 |
| WO | WO-2012109371 A2 | 8/2012 |
| WO | WO-2013025921 A1 | 2/2013 |
| WO | WO-2013060781 A1 | 5/2013 |
| WO | WO-2013060784 A1 | 5/2013 |
| WO | WO-2013060874 A1 | 5/2013 |
| WO | WO-2013098397 A2 | 7/2013 |
| WO | WO-2013126770 A1 | 8/2013 |
| WO | WO-2013138384 A2 | 9/2013 |
| WO | WO-2013148810 A1 | 10/2013 |
| WO | WO-2014037794 A2 | 3/2014 |
| WO | WO-2014054035 A1 | 4/2014 |
| WO | 2015062136 A1 | 5/2015 |
| WO | WO-2018154286 A1 * | 8/2018 ............. A24F 40/10 |
| WO | WO-2021011739 A1 * | 1/2021 |

OTHER PUBLICATIONS

Application and File History for U.S. Appl. No. 14/401,508, filed Nov. 14, 2014, Inventor: Lord, 496 pages.

Application and File History for U.S. Appl. No. 14/912,598, filed Feb. 17, 2016, Inventors: Lord et al., 370 pages.
Decision to Grant for Japanese Application No. 2015-537196, dated Jul. 6, 2017, 3 pages (6 pages with translation).
Decision to Grant for Japanese Application No. 2016537385, dated Sep. 27, 2017, 3 pages.
Decision to Grant dated Aug. 24, 2016 for Russian Application No. 201511435112, 12 pages.
Decision to Grant dated Jun. 24, 2016 for Russian Application No. 201415041912 (080853), 10 pages.
Examination Report No. 1 dated May 2, 2016 for New Zealand Application No. 717778, 4 pages.
Extended Report for European Application No. 13779773.4, dated Jun. 20, 2016, 2 pages.
Extended Report dated Aug. 15, 2016 for New Zealand Application No. 71778, 3 pages.
Extended Report dated Nov. 16, 2016 for New Zealand Application No. 717778, 1 page.
Extended Search Report for European Application No. 17192572.0, dated Mar. 14, 2018, 8 pages.
First Examination Report for Australian Application No. 2013261801, dated Jul. 10, 2015, 2 pages.
First Extended Report for Australian Application No. 2013331849, dated Dec. 1, 2015, 3 pages.
First Extended Report for Australian Application No. 2014333571, dated Nov. 25, 2016, 4 pages.
International Preliminary Report on Patentability for Application No. PCT/EP2013/059936, dated Apr. 23, 2014, 10 pages.
International Preliminary Report on Patentability for Application No. PCT/EP2013/059949, dated Sep. 5, 2014., 13 pages.
International Preliminary Report on Patentability for Application No. PCT/EP2013/059954, dated Jul. 10, 2014, 6 pages.
International Preliminary Report on Patentability for Application No. PCT/EP2013/071070, dated Nov. 21, 2014, 6 pages.
International Preliminary Report on Patentability for International Application No. PCT/EP2013/071070, dated Jun. 19, 2015, 13 pages.
International Preliminary Report on Patentability for PCT/GB2014/052625, dated Dec. 3, 2015, 22 pages.
International Preliminary Report on Patentability for PCT/GB2014/053027 dated Dec. 10, 2015, 19 pages.
International Search Report and Written Opinion for Application No. PCT/EP2013/059946, dated Sep. 18, 2013, 8 pages.
International Search Report and Written Opinion for Application No. PCT/EP2013/059949, dated Sep. 25, 2013, 7 pages.
International Search Report and Written Opinion for Application No. PCT/EP2013/059954, dated Sep. 25, 2013, 8 pages.
International Search Report and Written Opinion for Application No. PCT/EP2013/071070, dated Apr. 2, 2014, 6 pages.
International Search Report and Written Opinion of the International Searching Authority for Application No. PCT/GB2014/052625, dated Feb. 6, 2015, 17 pages.
International Search Report and Written Opinion of the International Searching Authority for PCT/GB2014/053027, dated Apr. 22, 2015, 13 pages.
"Load Detecting Power Supply," National Semiconductor RD-1066 Production Applications Design Center, Dec. 2008, 17 pages.
"Microcontroller," 2018, Retrieved from the Internet: URL: https://www.techopedia.com/definition/3641/microcontroller.
Office Action and Search Report for Chinese Application No. 201480047679.8, dated Jul. 14, 2017, 5 pages.
Office Action dated Mar. 21, 2016, for Chinese Application No. 201380025370.4, 23 pages.
Office Action dated May 4, 2016 Chinese Patent Application No. 201380025843.7, 25 pages.
Office Action dated Nov. 17, 2017 for Chinese Application No. 201480055728.2, 8 pages (20 pages with translation).
Office Action for Canadian Application No. 2,872,764, dated Aug. 31, 2016, 6 pages.
Office Action for Canadian Application No. 2,872,764, dated Oct. 5, 2015, 6 pages.
Office Action for Canadian Application No. 2,886,922, dated Mar. 4, 2016, 3 pages.

(56) References Cited

OTHER PUBLICATIONS

Office Action for Canadian Application No. 2,922,280, dated Jan. 20, 2017, 4 pages.
Office Action for Chinese Application No. 201380025370.4, dated Oct. 11, 2016, 3 pages (8 pages with translation).
Office Action for Chinese Application No. 201380025459.0, dated Feb. 14, 2016, 19 pages.
Office Action for Chinese Application No. 201380025459.0, dated Oct. 27, 2016, 19 pages.
Office Action for Chinese Application No. 201380054442.8, dated Jun. 28, 2017, 8 pages (20 pages with translation).
Office Action for Japanese Application No. 2015-537196, dated Mar. 22, 2016, 3 Pages (7 pages with translation).
Office Action for Japanese Application No. 2015-537196, dated Nov. 22, 2016, 4 pages (9 pages with translation).
Office Action for Japanese Application No. 2016537385, dated Mar. 3, 2017, 6 pages.
Office Action for Japanese Application No. 2017-153826, dated Jun. 19, 2018, 3 pages (6 pages with translation).
Office Action dated May 9, 2017 for Japanese Application No. 2016-520611, 13 pages.
Office Action dated Apr. 27, 2018 for Korean Application No. 20157010072,10 pages (19 pages with translation).
Office Action dated Aug. 11, 2016, for Korean Application No. 10-2014-7035205, 11 pages.
Office Action dated Aug. 7, 2017 for European Application No. 13779773, 2 pages.
Office Action dated Jul. 26, 2017, for Korean Application No. 10-2016-7009422,9 pages (with translation 17 pages).
Office Action dated May 26, 2017 for Korean Application No. 20147035025, 6 pages.
Office Action dated Sep. 23, 2016, for Korean Application No. 10-2014-7035201, 12 pages.
Search Report dated Aug. 8, 2016 for Russian Application No. 2014150420, 5 pages.
Search Report dated Feb. 21, 2017, for Japanese Application No. 2016-537385, 43 pages (56 pages with translation).
Search Report dated Mar. 27, 2018 for Russian Application No. 2016147728, 3 pages (6 pages with translation).
Search Report dated Mar. 28, 2017 for Japanese Application No. 2016-520611, 18 pages (with translation 46 pages).
Search Report dated Sep. 12, 2012 for Great Britain Application No. GB1208349.9, 1 page.
Second Examination Report for Australian Application No. 2013261801, dated Jun. 23, 2016, 3 pages.
Second Extended Report for Australian Application No. 2013331849, dated Feb. 5, 2016, 3 pages.
Second Extended Report for Australian Application No. 2014333571, dated Jan. 23, 2017, 4 pages.
Third Extended Report for Australian Application No. 2014333571, dated May 23, 2017, 4 pages.
Vaishali et al., "Random and Periodic Sleep Schedules for Target Detection in Sensor Networks", Journal of Computer Science and Technology, May 2008, vol. 23(3), pp. 343-354.
International Preliminary Report on Patentability received for PCT Patent Application No. PCT/GB2018/053684, completed on Apr. 3, 2020, 12 pages.
International Search Report and Written Opinion received for PCT Patent Application No. PCT/GB2018/053684, dated Mar. 13, 2019, 11 pages.

\* cited by examiner

ELECTRONIC AEROSOL PROVISION SYSTEM

PRIORITY CLAIM

The present application is a National Phase entry of PCT Application No. PCT/GB2018/053684, filed Dec. 19, 2018, which claims priority from GB Patent Application No. 1721821.5, filed Dec. 22, 2017, each of which is hereby fully incorporated herein by reference.

TECHNICAL FIELD

The present disclosure relates to aerosol provision systems such as nicotine delivery systems (e.g. electronic cigarettes and the like) and more specifically to a connector configured to be retrofitted to an electronic aerosol provision system.

BACKGROUND

Aerosol or vapor provision systems such as e-cigarettes generally comprise a reservoir of an aerosol precursor material containing a formulation, typically including nicotine, from which an aerosol is generated, such as through vaporization or other means. Thus an aerosol source for a vapor provision system may comprise a heating element or other aerosol generating component coupled to a portion of the aerosol precursor material from the reservoir. In some systems, the heating element and reservoir are comprised within a first section or component which is connectable to a second section or component housing a battery to provide electrical power to the heating element. In use, a user inhales on an aerosol outlet (mouthpiece) for the system while electrical power is supplied to the vaporizer. Air is drawn into the device through inlet holes and into a vapor generation chamber where the air mixes with the vaporized aerosol precursor material. There is a flow path connecting between the vapor generation chamber and the aerosol outlet so the incoming air drawn through the vapor generation chamber continues along the flow path to the mouthpiece opening, carrying some of the vapor with it for inhalation by the user.

There are a number of characteristics of an e-cigarette that may be considered by the user, wherein these characteristics are determined by the first section including the heating element, the second section housing the battery and any inbuilt functions that may be provided by the e-cigarette once the first section and the second section are combined. Each user has individual needs and preferences. This may result in some inbuilt functions not being used at all, where said inbuilt functions may continue using up the power that may otherwise be used by the e-cigarette. Further, providing inbuilt functions is difficult due to various challenges such as manufacturing complexity and the cost of manufacture. Thus, it is inefficient to provide an e-cigarette comprising inbuilt functions that are not used by the user.

Accordingly, approaches aimed at providing efficient aerosol provision system which also has the functionalities required by the user's needs or desires with increased versatility are of interest.

SUMMARY

According to one aspect of certain embodiments there is provided a connector configured to be retrofitted to an electronic aerosol provision system comprising: a first connecting interface connectable to a vaporizer for vaporizing liquid for inhalation by a user; a second connecting interface connectable to a power supply for supplying power to the vaporizer; a sensor for sensing a parameter indicative of a change in the electronic aerosol provision system; and a control unit connected to the sensor and configured to output a signal based on the information from the sensor, wherein the connector, when connected to a vaporizer and to a power supply, forms an electronic aerosol provision system.

The first connecting interface and the second connecting interface may comprise engagement mechanisms that are incompatible with each other, such that the connector is an adaptor configured to connect a vaporizer and a power supply which comprise engagement mechanisms that are incompatible with each other directly.

The control unit may be configured to adjust the amount of power supplied to the vaporizer based on the information from the sensor.

The control unit may be configured to remove connection between the power supply and the vaporizer based on the information from the sensor.

The sensor may be configured to sense a parameter indicative of a change in the vaporizer.

The sensor may comprise at least one of the following:
a pressure sensor located within the connector;
an airflow monitor;
a heat sensor;
a humidity sensor;
a pressure sensor located at an engagement interface of the connecting interfaces;
a power monitor configured to monitor the power supplied by a power supply and consumed by a vaporizer;
a biometric sensor; and
a vaporizer coil resistance sensor.

The pressure sensor located within the connector, the airflow monitor, the heat sensor and the humidity sensor may each be configured to sense a parameter indicative of inhalation by the user.

The heat sensor, the pressure sensor located at an engagement interface of the connecting interfaces, the power monitor and the motion sensor may each be configured to detect an electrical and/or mechanical connection of a component, which forms a part of the electronic aerosol provision system, to the connector. The component may be the vaporizer, the power supply, a mouthpiece connectable to the vaporizer or a mouthpiece cap connectable to the mouthpiece.

The pressure applied to the pressure sensor located at an engagement interface of the connecting interfaces may change as a final engagement arrangement at the connecting interfaces is reached.

The power monitor may comprise a voltage sensor and/or a current sensor.

The sensor may comprise a first heat sensor located closer to the first connecting interface than the second connecting interface and connected to the control unit.

The control unit may be configured to remove connection between the power supply and the vaporizer if an instant temperature value detected by the first heat sensor is higher than a predetermined threshold value.

The control unit may be configured to decrease the power supplied to the vaporizer if an instant temperature value detected by the second heat sensor is higher than a predetermined threshold value.

The sensor may further comprise a biometric sensor.

The biometric sensor may be configured to obtain information about the user, once it is determined that the connector is connected to a vaporizer and a power supply to form an electronic aerosol provision system by the control unit.

The control unit may be configured to determine that an inhalation has occurred when an instant value of the pressure sensor and/or the airflow monitor is higher than a predetermined threshold value; and/or when an instant value of the heat sensor and/or the humidity sensor is lower than a predetermined threshold value.

The control unit may be configured to control power to be supplied to the vaporizer based on the detection of connection of the component.

The control unit may be configured to cause power to be supplied to the vaporizer when it is detected that the pressure level sensed by the pressure sensor located at an engagement interface of the connecting interfaces is within a predetermined range.

The control unit may be configured to obtain signal from an aerosol provision system component detector located external to the connector. Such externally located component detector may be a mouthpiece detector or a mouthpiece cap detector.

The control unit may be configured to decrease the power to be supplied to the vaporizer if the power supplied by the power supply is larger than the power consumed by the vaporizer.

The output device may comprise at least one of:
a communication interface for providing wireless communications;
a communication interface for providing wired connections;
illumination means;
audio output device;
haptic output device.

The illumination means may be formed around a full perimeter of the connector.

The control unit may be configured to cause power to be supplied to the vaporizer in response to determination that an inhalation has occurred.

The control unit may be configured to cause power supplied to the vaporizer to decrease when a predetermined amount of time has passed from a detection of an inhalation.

The control unit may be configured to control the output of the output devices and/or control the power to be supplied to the output devices based on the inhalation detection information, such that the output devices indicate an amount of inhalation per inhalation (puff) and/or the changing amounts during a single inhalation (e.g. cumulative amount). The control unit may be configured to cause power supplied to the illumination means to decrease during the predetermined amount of time after the initial detection of an inhalation.

The control unit may be configured to control the output of the output device based on pressure level sensed, such that the output device indicates a stage of the engagement at the connecting interfaces.

The control unit may be configured to control the power supplied to the vaporizer based on the information detected by the sensor.

The control unit may be configured to output a signal to an output device and control the output device based on the information detected by the sensor.

The control unit may configured to determine, during use of the aerosol delivery device, usage characteristics of the aerosol delivery device based on the information detected by the sensor.

The connector may further comprise a memory configured to store, during use of the aerosol delivery device, information recording usage characteristics of the aerosol delivery device based on the information detected by the sensor.

The information recording usage characteristics of the aerosol delivery device may be communicated to a user or an external device via the output device.

The control unit may be configured to control the output device to indicate a state of the electronic aerosol provision system.

The connector may comprise an air channel for air inhaled by a user to flow through and out to the vaporizer when the connector is connected to the vaporizer and to the power supply.

The connector may comprise a user control operable by an actuating characteristic to allow the user to alter the level of airflow of inhaled air along the electronic aerosol provision system.

The connector may comprise a movable part that can be moved into and out of the airflow channel to change the size of the bore of the air channel at the location of the movable part.

The movable part may be directly accessible from the exterior of the connector such that the size of the bore of the air channel is modifiable by the user.

The movable part may be connected to a control which is accessible from the exterior of the connector such that it is modifiable by the user.

The control unit may be configured to control the power to be supplied to the output device based on the user control, such that the output device indicates the level of airflow through the connector.

The connector may comprise a user power control configured to alter the level of electrical power provided from the power supply to the vaporizer.

A variable resistor or a rheostat may be connected to the user power control.

The control unit may be connected to the user power control and configured to adjust the output of the output device based on the information from the sensor so as to reflect the level of power supplied to the vaporizer.

The control unit may be configured to alter the output of the output device when a mismatch is detected between the power supplied and the power consumed.

The control unit is configured to alter the output of the output device to reflect the level of voltage provided by the power supply to the vaporizer.

The connector may comprise a power source configured to power the control unit, the sensors and the output devices.

According to another aspect of certain embodiments there is provided an aerosol provision system comprising: a connector according to any of the passages above; a vaporizer connected to the connector; and a power supply connected to the connector.

According to yet another aspect of certain embodiments there is provided an aerosol provision system comprising a connector according to any of the passages above, a vaporizer connected to the connector, wherein the vaporizer comprises a mouthpiece for the user to contact when inhaling; a power supply connected to the connector; and a mouthpiece detector configured to send an electrical signal to the connector when a connection between the mouthpiece and the vaporizer is detected.

The mouthpiece detector may be a pressure sensor.

The mouthpiece detector may be located at the engagement interface between the mouthpiece and the vaporizer, and configured to send a signal to the connector when an instant pressure sensed is higher than a predetermined value.

The mouthpiece may comprise a control circuitry configured to send a signal when connected to the power supply.

A first portion of the mouthpiece detector may be located at the mouthpiece and a second portion of the mouthpiece detector may be located at the vaporizer, wherein the first portion and the second portion form an electrical connection when the mouthpiece and the vaporizer are connected.

The vaporizer may comprise a mouthpiece cover configured to engage with the mouthpiece to cover an air outlet formed on the mouthpiece and a mouthpiece cover detector configured to send a signal to the connector when a connection between the mouthpiece and the mouthpiece cover is detected.

The control unit of the connector may be configured to cause power to be supplied to the vaporizer only when a signal is received from the mouthpiece detector.

The control unit may be configured to cause power to be stopped from being supplied to the vaporizer when a signal is received from the mouthpiece cover detector.

The control unit may be configured to control the power to be supplied to the output device based on the signals received from the mouthpiece detector and/or the mouthpiece cover detector, such that the output device indicates a state of the engagement of the mouthpiece to the vaporizer and/or the engagement of the mouthpiece cover to the mouthpiece.

These and further aspects of certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, an electronic vapor provision device or a component for an electronic vapor provision device may be provided in accordance with approaches described herein which includes any one or more of the various features described below as appropriate.

BRIEF DESCRIPTION OF THE DRAWINGS

Embodiments of the disclosure will now be described, by way of example only, with reference to the accompanying drawings, in which.

DETAILED DESCRIPTION

Figure 1:
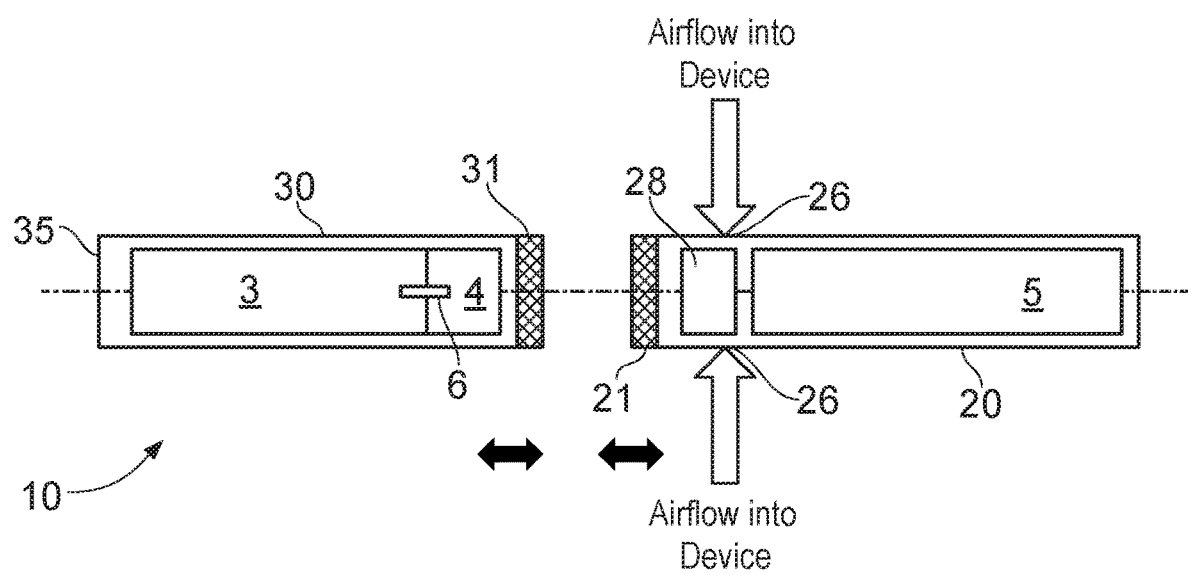
FIG. 1 shows a simplified schematic cross-sectional view of an example electronic cigarette or aerosol provision system.

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

As described above, the present disclosure relates to (but is not limited to) electronic aerosol or vapor provision systems, such as e-cigarettes. Throughout the following description the terms "e-cigarette" and "electronic cigarette" may sometimes be used; however, it will be appreciated these terms may be used interchangeably with aerosol (vapor) provision system or device. Similarly, "aerosol" may be used interchangeably with "vapor". As such, the systems of the present disclosure are not limited to the generation of aerosols via heating, but encompass aerosol generation via other means, such as vibration, electrostatic means, etc.

As used herein, the term "component" is used to refer to a part, section, unit, module, assembly or similar of an electronic cigarette that incorporates several smaller parts or elements, often within an exterior housing or wall. An electronic cigarette may be formed or built from a plurality of such components, and the components may be removably connectable to one another to define the whole electronic cigarette.

According to embodiments of the disclosure, there is provided an electronic connector configured to be retrofitted to an electronic cigarette, wherein the connector provides an additional functionality to the electronic cigarette. According to other embodiments of the disclosure, the connector also functions as an adaptor for connecting a vaporizer and a battery, wherein the vaporizer and the battery are not directly connectable to each other. Therefore, by using the connector, an additional functionality can be added to the electronic cigarette. In other cases, the connector may function as an adaptor for a vaporizer and a battery that are incompatible to each other to form an e-cigarette that was not intended at manufacture, wherein an additional functionality can be introduced at the same time. In this way, the user is provided with components for constructing a more versatile e-cigarette, through which the user is able to choose and combine various different functionalities and/or components of the e-cigarette according to their desire or needs. In one embodiment, the additional functionality is provision of illumination. In another embodiment, the additional functionality is provision of a safety feature relating to the power supply. In yet another embodiment, the additional functionality is provision of air flow variation control. In another embodiment, the additional functionality is detection of inhalation by the user. In another embodiment, the additional functionality is component detection prior to power supply. Various functionalities described in relation to each embodiment may be provided in combination or separately in a single connector or adaptor.

FIG. 1 is a highly schematic diagram (not to scale) of an example aerosol/vapor provision system such as an e-cigarette 10. The specific wiring and the shaping that provide the air flow path have been omitted from the figure for reasons of clarity. The e-cigarette 10 has a generally cylindrical shape, extending along a longitudinal axis indicated by a dashed line, and comprises two main components, namely a power component or section 20 and a cartridge assembly or section 30 (sometimes referred to as a cartomizer, clearomizer or atomizer) that operates as a vapor generating component.

The cartridge assembly 30 includes a reservoir 3 containing an aerosol precursor material such as a source liquid comprising a liquid formulation from which an aerosol is to be generated, for example containing nicotine. The reservoir 3 has the form of a storage tank, being a container or receptacle in which source liquid can be stored such that the liquid is free to move and flow within the confines of the tank. Alternatively, the reservoir 3 may contain a quantity of absorbent material such as cotton wadding or glass fiber which holds the source liquid within a porous structure. The reservoir 3 may be sealed after filling during manufacture so as to be disposable after the source liquid is consumed, or may have an inlet port or other opening through which new source liquid can be added. The cartridge assembly 30 also comprises an electrical heating element or heater 4 located externally of the reservoir tank 3 for generating the aerosol by vaporization of the source liquid by heating. A liquid flow path arrangement such as a wick or other porous element 6 may be provided to deliver source liquid from the reservoir 3 to the heater 4. The wick 6 has one or more parts located inside the reservoir 3 so as to be able to absorb source liquid and transfer it by wicking or capillary action to other parts of the wick 6 that are in contact with the heater 4. This liquid is thereby heated and vaporized, to be replaced by new source liquid transferred to the heater 4 by the wick 3. The wick therefore extends through a wall that defines the interior volume of the reservoir tank 3, and might be thought of as a bridge or conduit between the reservoir 3 and the heater 4.

A heater and wick (or similar) combination is sometimes referred to as an atomizer or atomizer assembly, and the reservoir with its source liquid plus the atomizer may be collectively referred to as an aerosol source. Various designs are possible, in which the parts may be differently arranged compared to the highly schematic representation of FIG. 1. For example, the wick 6 may be an entirely separate element from the heater 4, or the heater 4 may be configured to be porous and able to perform the wicking function directly (a metallic mesh, for example). Alternatively, the liquid conduit may be formed from one or more slots, tubes or channels between the reservoir and the heater which are narrow enough to support capillary action to draw source liquid out of the reservoir and deliver it for vaporization. Other means for vapor generation may be used in place of a heater, such a vibrating vaporizer based on the piezoelectric effect, for example. In general, therefore, an atomizer can be considered to be a vapor generating or vaporizing element able to generate vapor from source liquid delivered to it, and a liquid conduit (pathway) able to deliver or transport liquid from a reservoir or similar liquid store to the vapor generator such as by a capillary force. Embodiments of the disclosure are applicable to all and any such configurations.

Returning to FIG. 1, the cartridge assembly 30 also includes a mouthpiece 35 having an opening or air outlet through which a user may inhale the aerosol generated by the heater 4.

Figure 2:
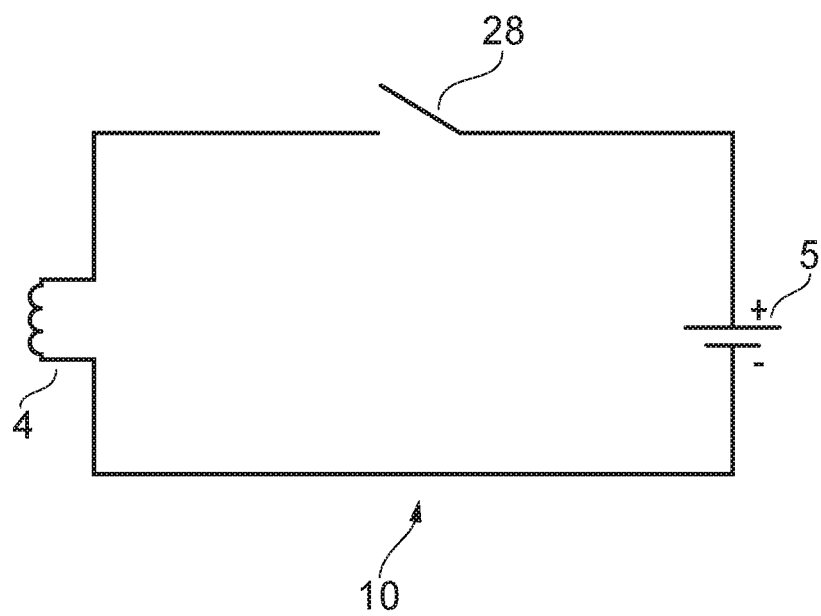
FIG. 2 shows a simplified circuit diagram of an example basic electronic cigarette or aerosol provision system.

The power component 20 includes a cell or battery 5 (referred to herein after as a battery 5, and which may be re-chargeable) to provide power for electrical components of the e-cigarette 10, in particular the heater 4. A basic e-cigarette includes the above described two portions and a simple on-off switch 28 which allows the user to turn the e-cigarette 10 on or off by connecting the heater 4 to the battery 5 when vapor is required. FIG. 2 is a simplified circuit diagram of said basic e-cigarette 10. The simple on-off switch 28 connects the battery 5 to the heater 4 when activated by the user.

It has been realized, however, that it may sometimes be desirable for the e-cigarette to comprise other functionalities for increased safety or to enhance the experience of the user. Where the e-cigarette 10 is manufactured to have such functions, on-off switch 28 may be replaced by a PCB and other relevant circuitries required to implement such functionalities. This will be discussed in further detail below.

When the heating element 4 receives power from the battery 5, the heating element 4 vaporizes source liquid delivered from the reservoir 3 by the wick 6 to generate the aerosol, and this is then inhaled by a user through the opening in the mouthpiece 35. The aerosol is carried from the aerosol source to the mouthpiece 35 along an air channel (not shown) that connects the air inlet 26 to the aerosol source to the air outlet when a user inhales on the mouthpiece 35. An air flow path through the electronic cigarette is hence defined, between the air inlet(s) (which may or may not be in the power component) to the atomizer and on to the air outlet at the mouthpiece. In use, the air flow direction along this air flow path is from the air inlet to the air outlet, so that the atomizer can be described as lying downstream of the air inlet and upstream of the air outlet.

In this particular example, the power section 20 and the cartridge assembly 30 are separate parts detachable from one another by separation in a direction parallel to the longitudinal axis, as indicated by the solid arrows in FIG. 1. The components 20, 30 are joined together when the device 10 is in use via the connecting interface 21, 31 (for example, a screw or bayonet fitting) which provide mechanical and electrical connectivity between the power section 20 and the cartridge assembly 30. This is merely an example arrangement, however, and the various components may be differently distributed between the power section 20 and the cartridge assembly section 30, and other components and elements may be included. The two sections may connect together end-to-end in a longitudinal configuration as in FIG. 1, or in a different configuration such as a parallel, side-by-side arrangement. The system may or may not be generally cylindrical and/or have a generally longitudinal shape. Either or both sections may be intended to be disposed of and replaced when exhausted (the reservoir is empty or the battery is flat, for example), or be intended for multiple uses enabled by actions such as refilling the reservoir and recharging the battery.

In some combinations of the cartridge assembly section 30 and the power section 20 used, in particular where the two sections were originally manufactured with the intention of being connected together to form an e-cigarette 10, the connecting interfaces 21 and 31 may be configured to cooperate with each other such that they are compatibly engageable. In some cases, however, the connecting interfaces 21 and 31 may be configured in such a way that they are unable to compatibly engage with each other, i.e. the connecting interface 21 and 31 may be incompatible with each other. For example, one of the connecting interfaces 21, 31 may be a screw and the other may be a bayonet fitting. Furthermore, as described above, often the PCB and circuitries required for implementing the functionalities are provided in the power section 20. Thus, where the user wishes to replace the power section 20 or use a different power section 20 whilst maintaining the cartridge section 30, any functionalities the e-cigarette 10 formed as a combination of the original power section 20 and the cartridge section 30 may be no longer be available. In other cases, no functionalities may have been available in the first place.

In this context, the present disclosure proposes a connector which enables additional functionalities to be implemented on an electronic cigarette once the connector is connected to a battery section and a cartridge to form the electronic cigarette. In some embodiments, the battery section and the cartridge may be incompatible with each other such that they cannot directly connect electrically and/or mechanically. Therefore the present disclosure offers a more versatile use of various electronic cigarette parts as well as providing increased functionality to an electronic cigarette without the need to obtain a new electronic cigarette comprising the desired inbuilt functionalities. Thus the user may combine various different electronic cigarette parts and functionalities in accordance with their requirements, which may even change with time and/or the user's experience with the e-cigarette 10. As only the functionalities required or wanted by the user may be provided with the e-cigarette 10, less power is wasted on functionalities that may not be desired or used by the user. Accordingly, a more efficient e-cigarette 10 may be provided.

Figure 3:
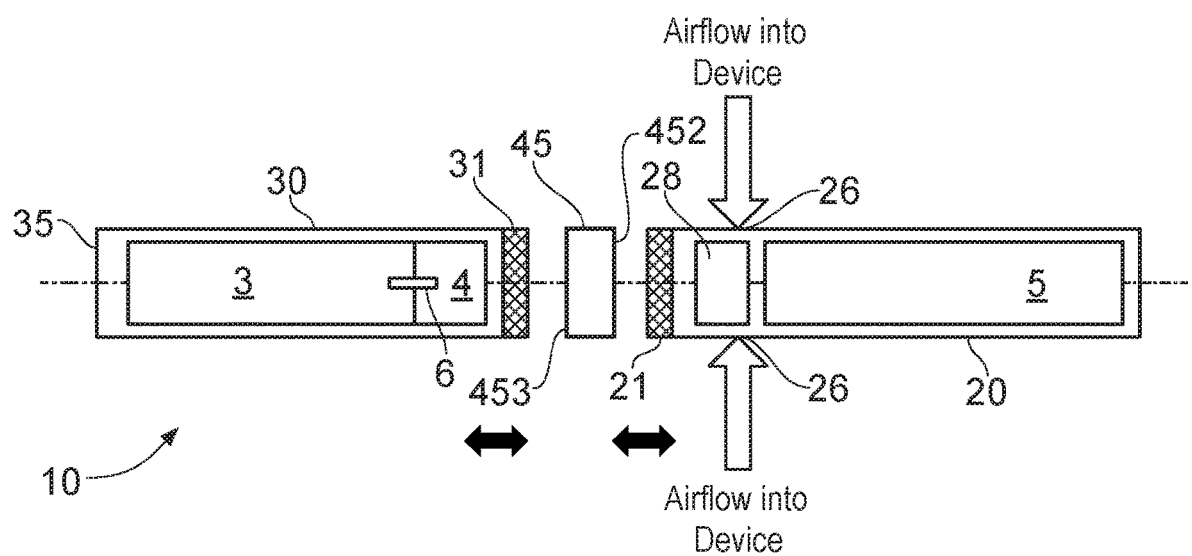
FIG. 3 shows a simplified schematic cross-sectional view of an example electronic cigarette or aerosol provision system with a connector configured to be retrofitted to the electronic cigarette or aerosol provision system according to an embodiment of the present disclosure.

FIG. 3 shows a simplified schematic cross-sectional view of an example electronic cigarette or aerosol provision system with a connector configured to be retrofitted to the electronic cigarette according to an embodiment of the present disclosure. In other words, the connector is an additional component which was not a part of the e-cigarette when the e-cigarette was originally manufactured. In this example, the e-cigarette as originally manufactured comprises only a simple on-off switch 28 without any further more advanced functionalities. The connecting interfaces 31 and 21 may or may not be directly connectable to each other (i.e. may or may not be compatible with each other directly). The connector 45 is disposed between the power section 20 and the cartridge assembly section 30 and has substantially the same diameter as the diameter of the power section 20 and of the cartridge assembly section 30. Hence, the exterior cylindrical surface of the e-cigarette 10 is continuous and largely uninterrupted by the connector 45. In other embodiments, particularly where the connector 45 comprises input methods for the user to adjust, such as user controls, the connector 45 may have a larger diameter such that the user controls protrude beyond the surface of the battery section 20 and/or the cartridge section 30 so as to enable easier handling and/or better gripping by the user. The connector comprises a control device 6, an output device 7 and an input device 8 which are configured to provide an additional functionality. These will be discussed in further detail below in relation to FIG. 5. As shown in FIG. 3, the connector 45 further comprises connecting interfaces 452 and 453 each respectively configured to connect to connecting interface 31 and connecting interface 21.

Where the connecting interfaces 21 and 31 are compatible with each other such that they may be directly connected to each other, the connector 45 is configured to comprise connecting interfaces 452 and 453 which are the same as connecting interfaces 31 and 21, respectively. That is to say, the connecting interface 453 which is configured to connect with connecting interface 31 has a connecting interface which is the same as connecting interface 21, and the connecting interface 452 which is configured to connect with connecting interface 21 has a connecting interface which is the same as connecting interface 31.

Where the connecting interfaces 21 and 31 are incompatible with each other such that it is not possible to directly connect the cartridge assembly section 30 and the power section 20, the connector is configured to comprise connecting interfaces 454 and 455 which are complementary female or male portions to the connecting interface 31 or 21, respectively. In other words, the connector 45 is configured to act as an adaptor 45. As such, the connector 45 may be referred to as a connector 45 or an adaptor 45. This is discussed in further detail below with reference to FIG. 4.

Where the power section 20 and the cartridge assembly section 30 were intended for use in combination at the time of manufacture, the connecting interfaces 21 and 31 would be male and female connectors, respectively, that are compatible with each other. In this case, the connector 45 is configured to have connecting interfaces which are essentially the same as the connecting interfaces 21 and 31.

Figure 4:
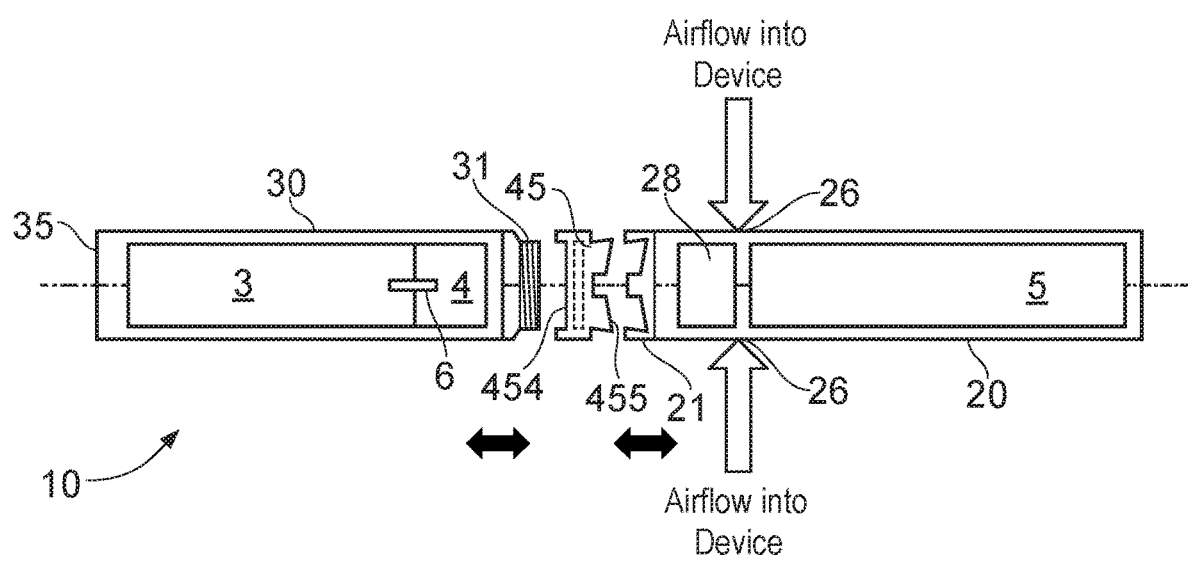
FIG. 4 shows a simplified schematic cross-sectional view of an example electronic cigarette or aerosol provision system with an adapter configured to be retrofitted to the electronic cigarette or aerosol provision system according to an embodiment of the present disclosure.

In some cases, however, the power section 20 and the cartridge assembly section 30 may not have been intended for use in combination at the time of manufacture. That is to say, the connecting interfaces 21 and 31 of the power section 20 and the cartridge assembly section 30, respectively, may be incompatible with each other and thus are unable to directly connect, as shown in FIG. 4. This situation may occur, for example, where the user wishes to use a new cartridge assembly section 30 or a new power section 20. The connector 45 may be configured to have connecting interfaces 454 and 455 in such a case, wherein the connecting interface 454 is configured to directly connect to the connecting interface 21 of the power section 20 and the connecting interface 455 is configured to directly connect to the connecting interface 31 of the cartridge assembly section 30.

For example, the connecting interface 21 of the power section 20 may comprise a standard 5-10 connector and the connecting interface 31 of the cartridge assembly section 30 may comprise a threaded connector. In such a case, the adaptor comprises a connecting interface 455, which is configured to directly connect to connecting interface 21, comprising a 5-10 connector receiving portion, and a connecting interface 454, which is configured to directly connect to connecting interface 31, comprising a threaded receiving portion. Other combinations of connecting portions may be implemented to join two incompatible interfaces together. For example, the interfaces may be formed of screw thread, bayonet, push fit or 5-10 connector. The combinations of connecting portions may be a combination of any two incompatible interfaces.

In another embodiment, a number of connectors or adaptors 45 may be used in combination, so as to implement a plurality of additional functionalities to the e-cigarette formed by connecting the cartridge assembly section 30 and the power section 20 using the combination of the connectors or adaptors 45.

In yet another embodiment, the adaptor connecting interfaces 454 and 455 may be formed as modular components that are releasably connected to the main functionality providing portion of the connector or adaptor 45, which comprises the control device 6, output device 7 and input device 8. As such, the user is able to select the required connecting interface 454 and 455 corresponding to the cartridge assembly section 30 and the power section 20, respectively, as well as the functionality desired and connect them to provide an e-cigarette which is formed of the desired cartridge assembly section 30, the power section 20 and the functionality providing adapter 45. For example, a plurality of connectors 45 which provide different functionalities may be connected between a battery and a cartridge.

In addition to allowing flexibility to the users, the connector or adaptor 45 also makes the manufacturing process more efficient in terms of both cost and productivity. Electronic aerosol provision systems are often subject to strict design constraints, especially with regard to the size of the system which can be governed by any number of factors and user requirements. Locating additional sensors and control devices within the device can be challenging owing to the fact that a suitably sized space for the sensors and the control devices must be allocated or found. This leads to an increase in the size of the device, or the sensor. In addition, the control devices may be located in an inconvenient place, which adds to the manufacturing complexity, potentially increasing costs. Thus, by providing the sensors and the control devices within a standalone device, such as a connector or adaptor, it is not necessary to adjust any existing manufacturing processes or to be overly restricted by the strict design constraints. All the while, it is possible to meet the requirements of the user with a greater flexibility.

The example devices shown in FIGS. 3 and 4 are presented in a highly schematic format to provide a high-level indication of the operation of an example electronic cigarette. No user operated controls such as input device 8 or output devices 7 are shown in FIG. 3.

Figure 5:
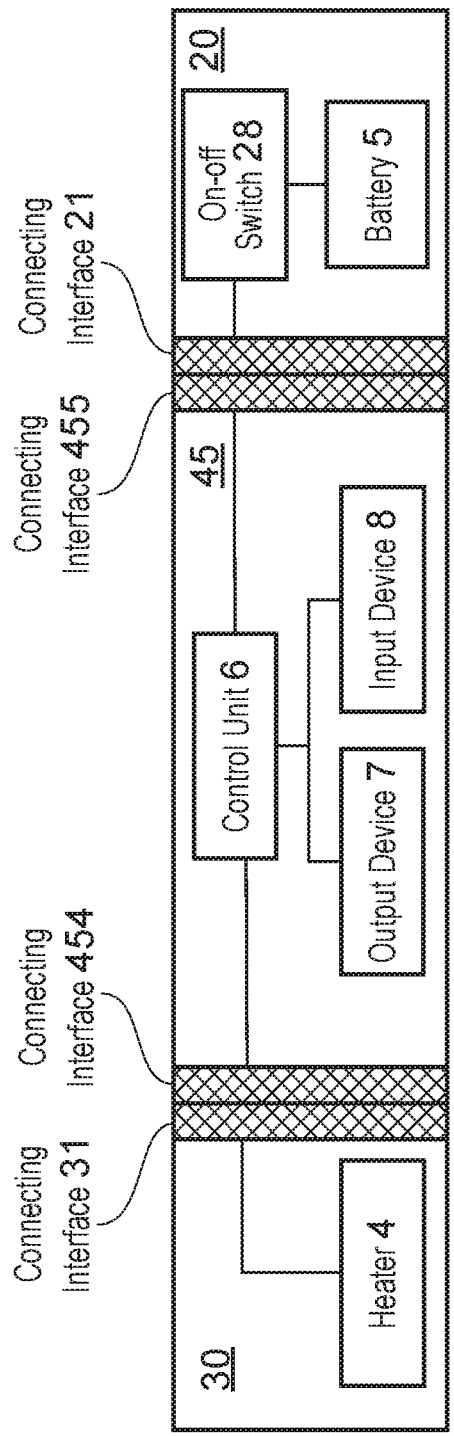
FIG. 5 is a block diagram of an example electronic cigarette or aerosol provision system comprising a connector according to an embodiment of the present disclosure.

FIG. 5 is a block diagram of an electronic cigarette comprising a connector or adaptor 45 according to an embodiment of the present disclosure.

As shown in FIGS. 3, 4 and 5, the connector or adaptor 45 is disposed between the power section 20 and the cartridge assembly section 30.

The connector 45 comprises connecting interfaces 454 and 455 or 453 and 452 for connecting with connecting interfaces 31 and 21, a control device 6, an output device 7 and an input device 8. The input device 8 may include a sensor and a user controller.

As described above, the connector 45 may provide one or more different functionalities. Some of the functionalities that may be provided by the connector (or adaptor) 45 are described below.

These various functionalities may be achieved by various arrangements and combinations of input devices 8 and output devices 7.

In one embodiment, the connector (or adaptor, depending on configuration of the connecting interfaces) 45 may be configured to provide an additional functionality of a safety feature for the power supply.

In this embodiment, the connector 45 is configured to limit the maximum electrical power that can be provided to the cartridge assembly section 30 by regulating the current or voltage, monitoring the total power or the temperature. This provides safety for the user in the event that the cartridge assembly section 30 is connected to a power section 20, with an unsuitably high power supply, which might damage or overheat the cartridge assembly 30.

In this embodiment, the control device 6 comprises a printed circuit board with a microcontroller for controlling the e-cigarette. The input device 8 comprises a power monitor configured to monitor the total power from the battery section 20 and the total power consumed by the vaporizer during use. By storing and comparing the power consumption in relation to the power supplied by the battery section 20, the control device 6 is able to determine whether the power supplied and the power consumed match or not. Where there is a mismatch, particularly where the power supplied by the battery section 20 is higher than the power consumed by the cartridge assembly 30, the control device 6 is configured to regulate the voltage or the current provided to the cartridge assembly 30.

The input device 8 may further comprise a user controller which enables the user to manually set the power provided by the power section 20 to the cartridge section 30. In this embodiment, the control device comprises a variable resistor which is connected to the user controller and changes the amount of voltage provided to the cartridge section 30 by the battery section 20.

In another embodiment, the input device 8 may comprise a temperature sensor, wherein in response to the temperature sensor detecting a temperature above a predetermined value, the control device 6 is configured to stop any further power being provided to the cartridge section 30, thus disabling the e-cigarette. As such, the on-off switch 28 may be overrun by the control device 6 and the safety feature can be achieved.

In another embodiment, the connector 45 may further comprise means for connecting with an external computing device, such as a smart phone. This may include components such as a USB connection port, or components which enable Bluetooth low energy connection. The user may be able to input the model of the cartridge assembly 30 and the power section 20 which they are using into the external computing device, and the control device 6 may be able to access data from the external device (e.g. a table of voltage limit data) to determine what power is optimal for the input model of cartridge assembly 30 and the power section 20.

The output device 7 may provide visible, audio and/or haptic output. For example, the output device 7 may comprise an illumination means. The illumination means is typically provided in the form of one or more light emitting diodes (LEDs), which may be the same or different colors (i.e. multi-colored). In the case of multi-colored LEDs, different colors are obtained by switching on red, green or blue LEDs, optionally at different relative brightness to give corresponding relative variations in color.

The output from the output device 7 may be used to signal to the user various conditions or states within the e-cigarette, such as a low battery warning. Different output signals may be used for signaling different states or conditions. For example, different colors, pulses of light or continuous illumination, different pulse durations, and so on may be assigned to respective conditions. The light may be utilized to show a low battery warning.

The LEDs may be provided around the entire perimeter of the adaptor, such that it is externally visible, when the connector 45 connects the cartridge section 30 to the battery section 20, regardless of the orientation of the adaptor 45 with respect to the cartridge assembly section 30 and the battery section 20. The LEDs forms a continuous ring around the perimeter. In other embodiments, the illumination means can be a plurality of closed spaced discrete lights arranged around the perimeter. The illumination is configured to indicate the operational states of the electronic cigarette. For example, in this embodiment the LEDs indicate when the control device is unable to determine the maximum power which should be supplied to the cartridge section 30. This alerts the user that it may not be safe to use the combination of the cartridge section 30 and the battery 20.

In another embodiment, the connector (or adaptor, depending on the configuration of the connecting interfaces) 45 is configured to provide an additional functionality of a voltage control by the user.

In this embodiment, the connector 45 comprises a user control configured to alter the level of electrical power provided from the battery 5 to the heater 4 or other vapor-generating element in the aerosol source. A higher power level produces an increased temperature rise at the heater 4 so that the amount of vapor generated is increased, and/or vapor generation is initiated sooner at the start of a heating cycle. For a given heater 4, the power level can be altered by changing the voltage applied across the heater 4, or by changing the current passed through the heater 4, or both, and the electrical cigarette 10 formed by connecting the connector 45 to the power section 20 comprising the battery 5 and the cartridge assembly section 30 comprising the heater 4 can be configured by the user accordingly.

In this embodiment, the input device 8 may comprise a user operable switch or dial for adjustment of the power level. For example, each position of a switch may make a different electrical connection between the battery and the heater that supplies a different power level, such as by connecting one out of a selection of differently valued resistors. A rheostat may alternatively be used to provide an adjustable resistance; this offers the benefit of allowing a continuous adjustment of resistance and hence power level, rather than a stepped adjustment corresponding to a set of different resistors. The user control may be configured to be adjustable over a continuous range, such as by rotation of a dial or sliding of a linear slider. Alternatively, the control may be configured such that its different positions each activate a different control signal sent to the control circuit of the electronic cigarette, and the control circuit (which may be programmable) is operable to modify the voltage or current supplied from the battery to the heater.

In this embodiment, the input device 8 comprises a control that modifies the electrical power supplied to the heater can be presented to the user directly as a power control, for example by labelling as a power control with an indication of the relative size of the possible settings (high to low, or 1 to 10, for example), or by labelling with numerical values of obtainable voltage, current or wattage. Knowledge of actual level of voltage, current or wattage by the user is not necessary for successful control of an electronic cigarette, but may be preferred by users of a scientific or technological bent.

In addition to control of the power level, for example a maximum value of power supplied to the heater, one might offer control of the cycle in which electrical power is provided to the heater. In some embodiment, the control device 6 is configured with a detailed power (heating) cycle or profile over which the power level alters, either per inhalation or over several inhalations. The cycle may include a pre-heat phase to bring the heater to vaporizing temperature, a heating phase when vapor is generated, and a cooling phase, for example (other and different cycles are known). Different heating cycles produce differently composed aerosol streams, so it may be desired to enable the user to choose between different cycles, as well as or instead of selecting a simple maximum power level or temperature. Accordingly, the input device 8 may comprise a user control for this, for example configured such that different positions of the control send different control signals to the control circuit, each of which activates heating according to a different cycle or profile.

Alternatively, the input device 8 may comprise a control that adjusts the electrical power as a temperature controller. A given power level produces a particular temperature output from the heater, so that altering the power and altering the temperature are effectively the same thing as regards operation of the electronic cigarette. The control might be labelled as a temperature control and marked as adjustable between high and low settings (in steps or continuously, for example) or a simple 1 to 10 scale. Alternatively, the scale might be marked with actual temperature values produced at each setting; these might indicate the heater temperature or the temperature of the inhaled aerosol.

Optionally, the output device 7 may provide visible, audio and/or haptic output. For example, the output device 7 may comprise an illumination means. The illumination means is typically provided in the form of one or more light emitting diodes (LEDs), which may be the same or different colors (i.e. multi-colored). In the case of multi-colored LEDs, different colors are obtained by switching on red, green or blue LEDs, optionally at different relative brightness to give corresponding relative variations in color.

The output from the output device 7 may be used to signal to the user various conditions or states within the e-cigarette, such as a low battery warning. Different output signals may be used for signaling different states or conditions. For example, different colors, pulses of light or continuous illumination, different pulse durations, and so on may be assigned to respective conditions. The light may be utilized to show a low battery warning.

The LEDs may be provided around the entire perimeter of the connector, such that it is externally visible, when the adaptor 45 connects the cartridge section 30 to the battery section 20, regardless of the orientation of the adaptor 45 with respect to the cartridge assembly section 30 and the battery section 20. The LEDs forms a continuous ring around the perimeter. In other embodiments, the illumination means can be a plurality of closed spaced discrete lights arranged around the perimeter. The illumination is configured to indicate the operational states of the electronic cigarette. For example, in this embodiment the LEDs indicate when the control device is unable to determine the maximum power which should be supplied to the cartridge section 30. This alerts the user that it may not be safe to use the combination of the cartridge section 30 and the battery 20.

In another embodiment, the connector (or adaptor, depending on the configuration of the connecting interface) 45 is configured to provide an additional functionality of a voltage control by the user.

In this embodiment, the input device 8 may comprise one or more controls which are configured to enable the user to modify the operation of the electronic cigarette, so that the aerosol output can be tailored to the user's particular requirements at any given time. A control may be configured to allow electronic/electrical adjustment of an operating parameter of the electronic cigarette. Movement of the control reconfigures electrical connections within the device or sends an electrical control signal to initiate operation at a particular level of a parameter. Alternatively, a control may be configured to allow mechanical adjustment of a component that modifies an operating parameter. Movement of the control may directly or indirectly move or reconfigure a mechanical part or parts within the device.

A first example of a user control is a control which allows the level of airflow along the air channel between the air inlet(s) and the air outlet to be altered. In this way, the amount of air which can be drawn through the device in an inhalation, and which is therefore available to collect vaporized source liquid, can be adjusted. The amount and/or concentration of vaporized source liquid per inhalation is hence controllable. Also, the amount of air per inhalation, or how hard the user must inhale to achieve a given airflow (also known as "resistance to draw"), can be a matter of personal preference that defines the experience of using the device for the user. Therefore, adjustability of this parameter allows customization of the device according to user preference.

A convenient way to provide for adjustment of the airflow level is to arrange for a movable part or parts that can be moved into and out of the airflow channel to change the size of the bore of the channel at the location of the movable part. The movable part may be directly accessible from the exterior of the electronic cigarette so that its position can be changed by the user, or may be connected to one or more other parts which can be externally adjusted by the user. The movable part may be located along the airflow channel at a point intermediate between the air inlet and the air outlet, or may be arranged to partly cover or uncover the air inlet(s). The user operable control is therefore configured such that actuation of the control produces movement of the movable part or parts into and out of the air flow channel (by directly or indirectly moving the movable part). Usefully, the restriction of the airflow channel bore enabled in this way is located upstream of the aerosol source to control the amount of air that collects vapor from the aerosol source.

Thus, the adaptor 45 may be configured to enable the airflow through the electronic cigarette to be varied by the user.

Optionally, the output device 7 may provide visible, audio and/or haptic output. For example, the output device 7 may comprise an illumination means. The illumination means is typically provided in the form of one or more light emitting diodes (LEDs), which may be the same or different colors (i.e. multi-colored). In the case of multi-colored LEDs, different colors are obtained by switching on red, green or blue LEDs, optionally at different relative brightness to give corresponding relative variations in color.

The output from the output device 7 may be used to signal to the user various conditions or states within the e-cigarette, such as a low battery warning. Different output signals may be used for signaling different states or conditions. For example, different colors, pulses of light or continuous illumination, different pulse durations, and so on may be assigned to respective conditions.

In this embodiment, different output signal of the LED can be used to illustrate different air flow status. For example, different color or brightness may be used to represent different level of air flow. The LEDs may be controlled by using the same controller varied by the user to vary the amount of air. As such, the changes to the level of air flow and the LEDs are controlled together and thus reflect the corresponding status.

The LEDs may be provided around the entire perimeter of the connector, such that it is externally visible, when the adaptor 45 connects the cartridge section 30 to the battery section 20, regardless of the orientation of the adaptor 45 with respect to the cartridge assembly section 30 and the battery section 20. The LEDs forms a continuous ring around the perimeter. In other embodiments, the illumination means can be a plurality of closed spaced discrete lights arranged around the perimeter. The illumination is configured to indicate the operational states of the electronic cigarette.

In another embodiment, the connector 45 is configured to detect inhalation by the user through the electronic cigarette and respond accordingly.

In this embodiment, the connector 45 is configured to turn on the cartridge assembly section 30 in response to detection of inhalation by the user.

The inhalation by the user is detected by the input device 8, which is located in the air flow path within the connector 45. In this embodiment, the input device 8 comprises a pressure sensor (not shown). The pressure sensor detects inhalation through the system 10 during which air enters through one or more air inlets 26 in the wall of the power section 20 by detecting a change in the pressure. A threshold value may be predetermined and pre-set, wherein an instant value obtained by the pressure sensor is compared against the threshold value to determine whether a pressure change detected is an inhalation by the user.

Alternatively, the input device 8 may be a heat detector which is configured to detect any change in the temperature of the air flow within the connector 45. As another alternative, the input device 8 may be a humidity detector to detect change in the humidity within the connector 45. The threshold values of the temperature and the humidity, against which an instant value obtained by the sensor is compared, may be predetermined and pre-set.

The control device 6 comprises a printed circuit board and/or other electronics or circuitry for controlling the e-cigarette. The control electronics/circuitry connect the heater 4 to the battery 5 when vapor is required, for example in response to a signal from the pressure sensor that detects inhalation through the system 10 as described above. The control device 6 is further configured to stop the power provided to the cartridge section 30 when no inhalation by the user is detected for a predetermined period of time.

Thus, the connector 45 enables the e-cigarette with inhalation detection functionality. As such, the battery is saved and no liquid source is vaporized unnecessarily.

The output device 7 may provide visible, audio and/or haptic output. For example, the output device 7 may comprise an illumination means. The illumination means is typically provided in the form of one or more light emitting diodes (LEDs), which may be the same or different colors (i.e. multi-colored). In the case of multi-colored LEDs, different colors are obtained by switching on red, green or blue LEDs, optionally at different relative brightness to give corresponding relative variations in color.

The output from the output device 7 may be used to signal to the user various conditions or states within the e-cigarette, such as a low battery warning. Different output signals may be used for signaling different states or conditions. For example, different colors, pulses of light or continuous illumination, different pulse durations, and so on may be assigned to respective conditions.

In this embodiment, different output signal of the LED can be used to illustrate whether the e-cigarette is on or off. For example, the LED may be set to be the brightest immediately after the detection of inhalation and dim as the time passes after the detection of inhalation. When the predetermined amount of time passes and thus the control device 6 is configured to stop power being supplied to the cartridge section 30, the LED is also configured to be turned off. Thus, the user is able to visually be informed as to when the e-cigarette has been turned off, and how long it will be until the heater 4 is turned off.

The LEDs may be provided around the entire perimeter of the connector, such that it is externally visible, when the adaptor 45 connects the cartridge section 30 to the battery section 20, regardless of the orientation of the adaptor 45 with respect to the cartridge assembly section 30 and the battery section 20. The LEDs forms a continuous ring around the perimeter. In other embodiments, the illumination means can be a plurality of closed spaced discrete lights arranged around the perimeter. The illumination is configured to indicate the operational states of the electronic cigarette.

In yet another embodiment, the connector 45 is configured to detect whether various components of the e-cigarette has been connected and respond accordingly.

In this embodiment, the connector 45 is configured to only turn on the cartridge assembly section 30 if an absence or presence of a predetermined component of the e-cigarette has been determined.

For example, the cartridge assembly section 30 may already comprise a mouthpiece detecting portion or a mouthpiece lid detecting portion. However, the user may wish to combine said cartridge assembly section 30 with a power section 20 which was not originally intended for use in combination with said cartridge assembly section 30. Accordingly, the power section 20 may not comprise the relevant circuitry for detecting the relevant components, in this case the mouthpiece and the mouthpiece lid. The control device 6 may use this detecting portion, which may already exist in some cartridge assembly sections 30, and use the input signal to determine whether power should be supplied to the cartridge assembly section 30 or not. The already existing detecting portion of the cartridge assembly section 30 may include a pressure sensor at the connecting portions of the cartridge assembly section 30 and the mouthpiece, which come into contact when the cartridge assembly section 30 and the mouthpiece are connected. Similarly, a pressure sensor may also be provided at the connecting portions of the mouthpiece and the mouthpiece lid which come into contact when the mouthpiece and the mouthpiece lid are connected. The input signals from the pressure sensors are provided to the control device 6, which is configured to only allow power to be provided to the cartridge assembly section 30 when the presence of the mouthpiece and the absence of the mouthpiece lid are detected.

Alternatively, the input device 8 may comprise pressure sensors located at the connecting interfaces 454, 455 or 452, 453, where the connecting interfaces 31 and 21 come into contact. The control device 6 is configured to determine when the pressure level between the connecting interfaces reaches the optimal value. A predetermined and pre-set threshold value may be stored in the control device 6, wherein the control device 6 compares an instant value of the pressure sensor to the threshold value to determine whether the connection between the connector 45 and the cartridge assembly section 30 and the power section 20 are optimal or not.

The output device 7 may provide visible, audio and/or haptic output. For example, the output device 7 may comprise an illumination means. The illumination means is typically provided in the form of one or more light emitting diodes (LEDs), which may be the same or different colors (i.e. multi-colored). In the case of multi-colored LEDs, different colors are obtained by switching on red, green or blue LEDs, optionally at different relative brightness to give corresponding relative variations in color.

The output from the output device 7 may be used to signal to the user various conditions or states within the e-cigarette, such as overly tight connections between the connector 45 and the power section 20 and the cartridge assembly section 30. Different output signals may be used for signaling different states or conditions. For example, different colors, pulses of light or continuous illumination, different pulse durations, and so on may be assigned to respective conditions.

In this embodiment, different output signal of the LED can be used to illustrate whether the connections forming the e-cigarette is optimal or overly tight. In other words, the LED may indicate to the user when the connecting interfaces 31, 21, 454, 455 are connected at optimal strength. The connecting interfaces 31, 21,454, 455 can be damaged in some cases when the user attempts to connect the connector 45 to the cartridge assembly section 30 and the battery section 20 using a force exceeding that necessary for the connecting interfaces 31, 21, 454, 455 to properly form mechanical and electrical engagements. Thus, overly tight engagements can damage the electrical and mechanical connections and is not desirable. A red LED may be turned on by the control device 6 when a high pressure level is detected. Thus, the user is able to visually be informed as to whether the connections are optimal. For example, one LED may be located closer to the power section 20 and another LED may be located closer to the cartridge assembly section 30. In this case, each LED may reflect the pressure level at each of the connecting interfaces 21 and 31. Thus, the user is able to visually be informed as which connection needs to be altered.

The LEDs may be provided around the entire perimeter of the connector, such that it is externally visible, when the adaptor 45 connects the cartridge section 30 to the battery section 20, regardless of the orientation of the adaptor 45 with respect to the cartridge assembly section 30 and the battery section 20. The LEDs forms a continuous ring around the perimeter. In other embodiments, the illumination means can be a plurality of closed spaced discrete lights arranged around the perimeter. The illumination is configured to indicate the operational states of the electronic cigarette.

The connector 45 may be configured to prevent the cartridge assembly section 30 being powered by the battery section 20 in the event that the electronic cigarette is improperly configured for safe operation, by checking for the presence or absence of one or more components. For example, the connector 45 may allow power to the cartridge assembly section 30 only when a mouthpiece component is coupled to the cartomizer, or only when a mouthpiece cover has been removed from the mouthpiece.

Thus, according to the present disclosure a single e-cigarette which comprises all the characteristics that are required or desired by the user may be provided with flexibility and efficiency.

Embodiments of the disclosure are not limited to the formats and configurations of functionalities described thus far. Other functionalities may also be implemented by a connector or adaptor to allow greater flexibility to the users without any changes from being made to the original e-cigarette components While the above described embodiments have in some respects focused on some specific example aerosol provision systems, it will be appreciated the same principles can be applied for aerosol provision systems using other technologies. That is to say, the specific manner in which various aspects of the aerosol provision system function are not directly relevant to the principles underlying the examples described herein.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc. other than those specifically described herein, and it will thus be appreciated that features of the dependent claims may be combined with features of the independent claims in combinations other than those explicitly set out in the claims. The disclosure may include other inventions not presently claimed, but which may be claimed in future.

The invention claimed is:

1. A connector configured to be retrofitted to an electronic aerosol provision system, the connector comprising:
    a first connecting interface connectable to a vaporizer for vaporizing liquid for inhalation by a user;
    a second connecting interface connectable to a power supply for supplying power to the vaporizer;
    a sensor for sensing a parameter indicative of a change in the electronic aerosol provision system; and
    a control unit connected to the sensor and configured to output a signal based on information from the sensor,
    wherein the connector, when connected to the vaporizer and to the power supply, forms the electronic aerosol provision system.

2. The connector according to claim 1, wherein the first connecting interface and the second connecting interface comprise engagement mechanisms that are incompatible with each other, such that the connector is an adaptor configured to connect the vaporizer and the power supply which comprise engagement mechanisms that are incompatible with each other directly.

3. The connector according to claim 1, wherein the parameter is indicative of a change in the vaporizer.

4. The connector according to claim 1, wherein the sensor comprises at least one of the following:
    a pressure sensor located within the connector;
    an airflow monitor;
    a heat sensor;
    a humidity sensor;
    a pressure sensor located at an engagement interface of the first connecting interface and the second connecting interface;
    a power monitor configured to monitor the power supplied by a power supply and consumed by the vaporizer; and
    a vaporizer coil resistance sensor.

5. The connector according to claim 1, wherein the control unit is configured to control the power supplied to the vaporizer based on the information from the sensor.

6. The connector according to claim 1, wherein the control unit is configured to output the signal to an output device and control the output device based on the information from the sensor.

7. The connector according to claim 6, wherein the output device comprises at least one of:
    a communication interface for providing wireless communications;
    a communication interface for providing wired connections;
    illumination means;
    an audio output device;
    a haptic output device.

8. The connector according to claim 1, wherein the control unit is configured to determine, during use of the electronic aerosol provision system, usage characteristics of the electronic aerosol provision system based on the information from the sensor.

9. The connector according to claim 8, comprising a memory configured to store, during use of the electronic aerosol provision system, information recording usage characteristics of the electronic aerosol provision system based on the information from the sensor.

10. The connector according to claim 8, wherein the control unit is configured to output the signal to an output device and control the output device based on the information from the sensor, and wherein the information recording usage characteristics of the electronic aerosol provision system is communicated to the user or an external device via the output device.

11. The connector according to claim 10, wherein the control unit is configured to control the output device to indicate a state of the electronic aerosol provision system.

12. The connector according to claim 1, comprising an air channel for air inhaled by the user to flow through and out to the vaporizer when the connector is connected to the vaporizer and to the power supply.

13. The connector according to claim 12, comprising a user control operable by an actuating characteristic to allow the user to alter a level of airflow of inhaled air along the electronic aerosol provision system.

14. The connector according to claim 13, comprising a movable part that can be moved into and out of the air channel to change a size of a bore of the air channel at a location of the movable part.

15. The connector according to claim 14, wherein the movable part is directly accessible from an exterior of the connector such that the size of the bore of the air channel is modifiable by the user.

16. The connector according to claim 14, wherein the movable part is connected to a user control which is accessible from an exterior of the connector such that the control is modifiable by the user.

17. The connector according to claim 16, wherein the control unit is configured to control the power to be supplied to the output device based on the user control, such that the output device indicates a level of airflow through the connector.

18. The connector according to claim 1, wherein the control unit is configured to obtain a signal from an external sensor located external to the connector.

19. An electronic aerosol provision system comprising:
    the connector according to claim 1;
    the vaporizer connected to the connector; and
    the power supply connected to the connector.

* * * * *